United States Patent [19]

Brimhall et al.

[11] Patent Number: 4,854,170

[45] Date of Patent: Aug. 8, 1989

[54] APPARATUS AND METHOD FOR USING ULTRASOUND TO DETERMINE HEMATOCRIT

[75] Inventors: Owen D. Brimhall, West Valley City; Stephen C. Peterson, Salt Lake City; Charles D. Baker, Sandy; Merwyn D. Riddle, Salt Lake City, all of Utah

[73] Assignee: Separation Technology, Inc., Salt Lake City, Utah

[21] Appl. No.: 256,731

[22] Filed: Oct. 12, 1988

[51] Int. Cl.$^4$ .................................... G01N 29/00
[52] U.S. Cl. ........................................ 73/570; 73/24; 210/748
[58] Field of Search .................... 73/570, 24, 61.4; 210/748; 356/40

[56] References Cited

U.S. PATENT DOCUMENTS

| | | | |
|---|---|---|---|
| 4,055,491 | 10/1977 | Porath-Furedi | 210/748 |
| 4,280,823 | 7/1981 | Szonntagh | 73/24 |
| 4,673,512 | 6/1987 | Schram | 210/748 |
| 4,743,361 | 5/1988 | Schram | 210/748 |

Primary Examiner—Tom Noland
Assistant Examiner—Louis M. Arana
Attorney, Agent, or Firm—J. Winslow Young

[57] ABSTRACT

This invention is an ultrasound apparatus for determining hematocrit. A sample of blood in a microhematocrit capillary tube is acoustically coupled to an ultrasound transducer which creates a standing wave in the blood sample. Red blood cells in the blood sample are packed in bands that correspond to the nodes of the standing wave. The thickness of the bands as a function of the thickness of the remaining plasma is an indication of the hematocrit of the blood sample.

7 Claims, 1 Drawing Sheet

APPARATUS AND METHOD FOR USING ULTRASOUND TO DETERMINE HEMATOCRIT

BACKGROUND

1. Field of the Invention

This invention relates to an apparatus and method for determining the hematocrit reading of a blood sample and, more particularly, to the use of ultrasound to cause rapid separation of red blood cells from plasma in the blood sample, the separation being in the form of bands which provide a directly readable indication of the hematocrit of the blood sample.

2. The Prior Art

Hematocrit is a measure of the volume fraction that red blood cells occupy in the blood. Conventionally, hematocrit has been determined by subjecting a blood sample to very high gravitational forces in a high speed centrifuge apparatus for several minutes. The incrementally greater density differential of the red blood cells causes them to pack into the lower part of the sample holder under centrifugation.

A drop of blood is drawn by capillary action into a microhematocrit capillary tube, the end of which is then plugged with a clay-like material. Under centrifugation separation occurs with the red blood cells becoming packed into the lower end of the tube with the plasma being displaced toward the top of the tube. The hematocrit is calculated by determining the ratio of the length of the red blood cell volume to the total length of the blood sample times one hundred.

Blood loss, whether through trauma, gastrointestinal bleeding, or during surgery can be discovered promptly if the medical personnel have immediate access to hematocrit readings that are rapidly obtainable and accurate. Current methods of measuring hematocrit require five to ten minutes and involve access to the necessary centrifuge apparatus. Accordingly, emergency medical personnel such as civilian paramedics and military medics do not currently obtain hematocrit information in the field while treating trauma cases because a) the current method using centrifugation is time consuming and fairly labor intensive, and b) the required high speed centrifuge apparatus is a poor candidate for field use since it is expensive, bulky, heavy, and yet fragile.

Additionally, the treatment of a trauma or gastrointestinal bleeding case in a hospital is not satisfactory since even an emergency or "stat hematocrit" requires at least five minutes centrifugation in conjunction with significant technician time and labor. Due to the cost of the centrifugation apparatus they are also placed in centralized locations. The end result is an additional time increment is required (beyond the centrifugation time) to transfer the microhematocrit capillary tube containing the sample to the centrifuge and then transmit the resulting hematocrit reading back to the medical personnel. This time factor is further compromised severely by the fact that in an endeavor to save technician labor several samples will be collected over a period of time so that all these samples can be processed in the centrifugation apparatus at the same time.

In view of the foregoing it would be a significant advancement in the art to provide a fast, convenient apparatus and method for rapid determination of hematocrit. An even further advancement would be to have a rapid hematocrit that could easily become a commonly gathered patient parameter so that medical personnel could be alerted early to the medical needs of a trauma patient particularly in cases of internal bleeding. Advantageously, such a device could become a commonly carried physician tool so that the physician could obtain his own hematocrit reading instead of sending the blood sample to the lab and waiting to obtain the hematocrit reading therefrom. Such a novel apparatus and method is disclosed and claimed herein.

BRIEF SUMMARY AND OBJECTS OF THE INVENTION

This invention relates to an ultrasound apparatus and method for separating red blood cells from the plasma in a blood sample to thereby provide a rapid hematocrit of the blood sample. A standing wave ultrasound field is imposed on the blood sample in a microhematocrit capillary tube and forces the red blood cells into tightly packed bands. This separation phenomena occurs within seconds and provides a rapid, accurate hematocrit of a blood sample.

It is, therefore, a primary object of t his invention to provide improvements in apparatus for determining hematocrit of a blood sample.

Another object of this invention is to provide improvements in the methods for determining hematocrit.

Another object of this invention is to provide ultrasound apparatus for separating a blood sample into alternating bands of packed red blood cells and plasma, the ratio of the total packed red blood cell volume to the volume of the blood sample being equal to the hematocrit of the blood sample.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENTS

Figure 1:
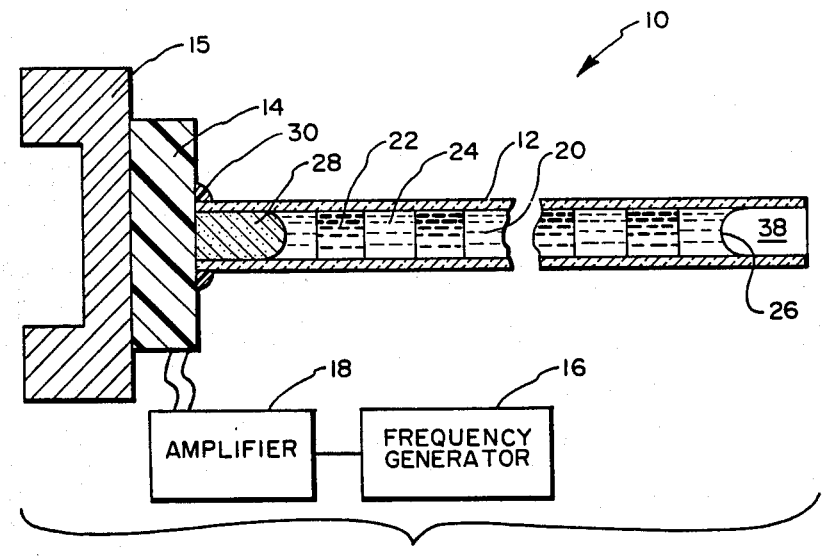
FIG. 1 is an enlarged, cross sectional view of a microhematocrit capillary tube in contact with an ultrasound transducer, the blood sample in the tube being illustrated schematically as having been banded by ultrasound energy.

The invention is best understood by reference to the drawing wherein like parts are designated by like numerals throughout in conjunction with th following description.

GENERAL DISCUSSION

We have found that an operating frequency of an ultrasound transducer in the range of one megahertz (1 MHz) will produce standing wave nodes and antinodes every 375 micrometers. Accordingly, at an hematocrit of 50% a blood cell band will be 375 micrometers wide and so will the plasma band be 375 micrometers wide. Correspondingly, an hematocrit of 25% will produce a blood cell band that is 190 micrometers wide and a plasma band that is about 560 micrometers wide.

It has been known for at least fifteen years that red blood cells can be forced into "bands" when exposed to an ultrasonic standing wave field. This banding phenomena imparts a striated appearance to the blood. The banding or striation in the blood is caused by standing waves that force the blood cells into the pressure minima of the acoustic field so that bands or striations form at half wavelength intervals.

The force exerted on a particle in an acoustic standing wave is given by the following formula:

$$Fa = \frac{Vo\, Pa^2\, KGin\, 2kz}{4\rho c^2} \left[ \frac{1}{\delta\sigma^2} - \left( \frac{5\delta - 2}{2\delta + 1} \right) \right] \quad (1)$$

where Vo is the particle volume, Pa is the pressure amplitude, $k=2\pi/\lambda$, $\sigma=c^*/c$, $\delta=\rho^*/\rho$, $c^*$ and $c$ are the sound velocities in the liquid driplet and medium while $\rho^*$ and $\rho$ are the densities of the liquid droplet and suspending medium, respectively.

The ultrasonic standing wave force $F_a$, as evidenced by equation (1), is a function of the particle volume, the pressure amplitude, the wave number, and the properties of the cells and the medium. This force is quite powerful and blood will form into "bands" within seconds after application of the acoustic field. The force $F_a$ "packs" the red blood cells very tightly together, just as a high speed centrifuge "packs" red blood cells into the bottom of a capillary tube. Accordingly, it is possible to use an ultrasonic standing wave to create a packed blood fraction which can then be measured as a function of the blood hematocrit reading.

DETAILED DESCRIPTION

Referring now more particularly to FIG. 1, the apparatus for using ultrasound to determine hematocrit is shown generally at 10 and includes a microhematocrit capillary tube 12, an ultrasound transducer 14, a heat sink 15, a frequency generator 16 and an amplifier 18. Microhematocrit capillary tube 12 is a conventional capillary tube having a hollow throughbore 38 into which a sample of blood 20 is drawn by capillary action. Blood 20 forms a meniscus 26 at one end. After intake of blood 20 into microhematocrit capillary tube 12 the other end is sealed with a putty-like sealant 28. Sealant 28 is any suitable, conventional sealant compound well-known in the art. Importantly, the sealed end of microhematocrit capillary tube 12 is acoustically coupled to ultrasound transducer 14 by a coupling medium 30 which can be any suitable ultrasonic coupling medium such as an acoustical gel, water, sealant 28, oil, or the like. Coupling medium 30 assures an adequate coupling of ultrasound energy (illustrated schematically at 32, FIG. 2) into blood 20.

Ultrasound transducer 14 is any suitable ultrasound transducer capable of generating the desired ultrasound energy in the preferred frequencies and at the selected power levels to accomplish the banding of blood 20 into bands of packed red blood cells 22 separated by bands of plasma 24. Heat sink 15 dissipates heat generated during operation of ultrasound transducer 14. The frequency generator 16 and amplifier 18 are used to drive ultrasound transducer 14 and can be any suitable system. In one embodiment, a small (approximately 1 cm square). ultrasound transducer 14 was selected from a high-impedance transducer material and was driven at a frequency of 1.0 MHz to cause distinct banding of blood 20 in 5 to 7 seconds in microhematocrit capillary tube 12. Typical power levels for ultrasound transducer 14 to create the desired levels of banding in blood 20 are about 1.0 watt/cm$^2$. Assuming a 1 cm$^2$ transducer, a 50% power conversion at ultrasound transducer 14, and a 12 volt battery in frequency generator 16, then 167 mA of current will be needed to drive the system. A 6 volt battery would be required to produce 333 mA.

Figure 2:
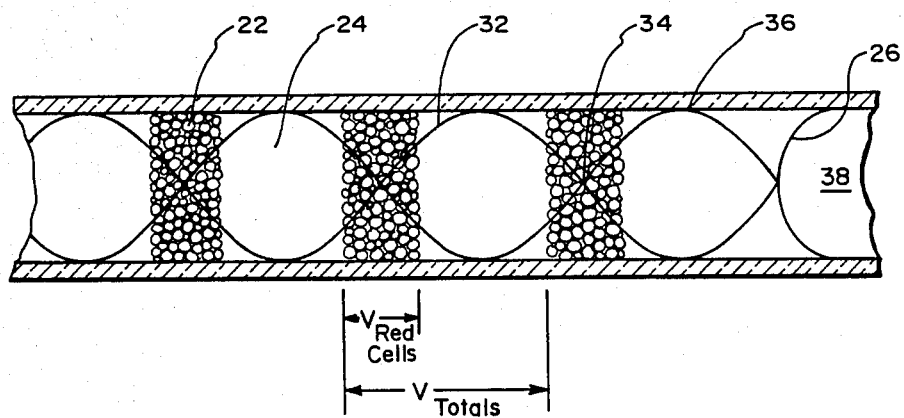
FIG. 2 is an enlargement of a portion of the microhematocrit capillary tube of FIG. 1 with a schematic illustration of the ultrasound waves in the blood sample.

Referring now to FIG. 2, an enlarged schematic of a portion of microhematocrit capillary tube 12 is shown having packed red blood cells in bands 22 separated by plasma bands 24. These alternate bands have been created in a standing wave field generated by ultrasound transducer 14 (FIG. 1). Standing waves 32 are created when the ultrasound energy strikes meniscus 26 (which acts as an air reflector) to create the standing wave represented by nodes 34 separated by antinodes 36. As schematically illustrated in FIG. 2, red blood cells are packed in bands 22 that correspond with the nodes 34 leaving plasma 24 in bands that generally correspond to antinodes 36.

Standing wave 32 can be quite powerful and will force blood cells into bands 22 within seconds after power is applied to ultrasound transducer 14. Experimentally, we have found that bands 22 comprise very tightly packed red blood cells just as high speed centrifugation forces red blood cells tightly together in the bottom of a microhematocrit capillary tube. Accordingly, the theoretical basis for the rapid hematocrit determination using an ultrasound apparatus to determine hematocrit 10 relies on a predictable relationship between the thickness of the ultrasonically induced blood bands 2 and the hematocrit of blood sample 20.

Figure 3:
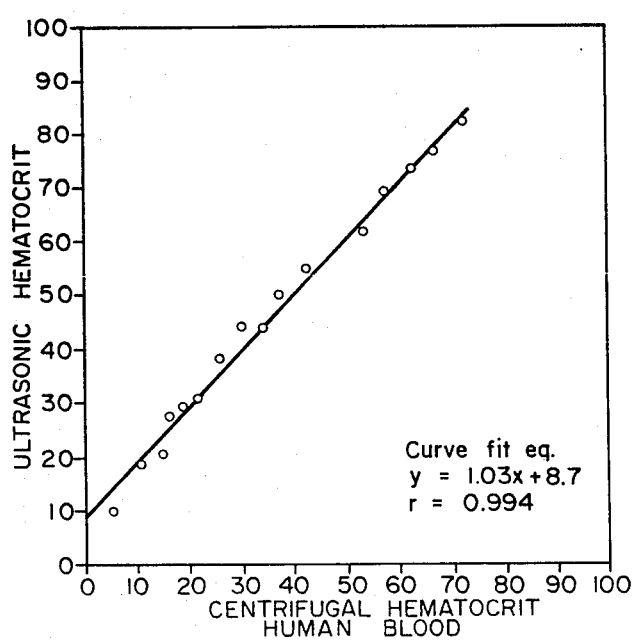
FIG. 3 is a graphical comparison of a hematocrit obtained using ultrasound versus a hematocrit using conventional centrifugation.

Referring now to FIG. 3 a comparison was made between the hematocrit of human blood obtained using conventional centrifugation techniques versus the apparatus using ultrasound to determine hematocrit 10. Advantageously, there is excellent correlation between the two systems over a wide range of hematocrit readings.

The Method

In order to determine hematocrit, a blood sample 20 is drawn into microhematocrit capillary tube 12 by capillary action. This is done by placing the tip of microhematocrit capillary tube against a drop of blood (not shown) allowing the capillary action to draw blood sample 20 into place forming meniscus 26. The intake end of microhematocrit capillary tube 12 is then sealed with a sealant 28 by punching it into a body of sealant (not shown). The sealed tip of microhematocrit capillary tube 12 is acoustically coupled with acoustic coupling medium 30 to ultrasound transducer 14. The preselected frequency is selected on frequency generator 16 and the signal produced thereby is amplified by amplifier 18 to drive ultrasound transducer 14.

Ultrasound energy in the form of a wave 32 is formed in blood sample 20 and is reflected by the air reflector of meniscus 26 to create the standing, acoustic wave 32 shown in FIG. 2. The red blood cells 22 are packed into the nodes 34 of standing, acoustic wave 32 while the plasma separates out as bands 24 that generally correspond to the antinodes 36. This phenomena occurs rapidly, generally on the order of about 5–7 seconds.

Accordingly, this invention provides a very rapid apparatus and method for using ultrasound to determine hematocrit. The close correlation between the hematocrit obtained using the ultrasound hematocrit apparatus 10 as compared to conventional centrifugation apparatus is clearly shown by the chart of FIG. 3.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for determining hematocrit comprising:
   a microhematocrit capillary tube;
   a blood sample in the microhematocrit capillary tube;
   an ultrasound transducer for producing ultrasound energy;
   a frequency generator means for generating a preselected frequency signal for the ultrasound transducer;
   amplifier means for amplifying the frequency signal from the frequency generator and transmitting the amplified signal to the ultrasound transducer;
   coupling means for coupling the ultrasound energy from the ultrasound transducer into the blood sample; and
   a meniscus formed at the end of the blood sample, the meniscus forming a reflector for ultrasound energy in the blood sample thereby creating a standing wave in the ultrasound energy in the blood sample.

2. The apparatus defined in claim 1 wherein the ultrasound transducer includes a heat sink for dissipating heat generated in the ultrasound transducer by the amplified signal.

3. The apparatus defined in claim 1 wherein the microhematocrit capillary tube includes a plug and the plug comprises the coupling means.

4. An apparatus for using ultrasound to determine hematocrit comprising:
   a microhematocrit capillary tube;
   a sample of blood in the microhematocrit capillary tube, the sample of blood being drawn by capillary action into a first end of the microhematocrit capillary tube;
   a meniscus in said sample of blood at a second end of the microhematocrit capillary tube;
   an ultrasound transducer means for producing ultrasonic energy;
   a frequency generator means for generating an ultrasound frequency signal for the ultrasound transducer;
   an amplifier means for amplifying the ultrasound frequency signal from the frequency generator means and connector means for connecting the amplified ultrasound frequency signal into the ultrasound transducer to produce said ultrasonic energy;
   coupling means for coupling the ultrasonic energy into the blood sample; and
   reflector means in said blood sample for creating a standing wave in said blood sample, said reflector means comprising said meniscus, the meniscus reflecting the ultrasonic energy to create said standing wave in the blood sample.

5. The apparatus defined in claim 4 wherein the ultrasound transducer includes a heat sink for dissipating heat generated in the ultrasound transducer by the amplified signal.

6. The apparatus defined in claim 4 wherein the microhematocrit capillary tube includes a plug and the plug comprises the coupling means.

7. A method for using ultrasound to determine hematocrit comprising:
   obtaining an ultrasound transducer;
   providing an ultrasound frequency generator;
   connecting an amplifier between the ultrasound frequency generator and the ultrasound transducer thereby amplifying for the ultrasound transducer a signal from the ultrasound frequency generator;
   selecting a microhematocrit capillary tube;
   drawing a sample of blood by capillary action into a first end of the microhematocrit capillary tube;
   forming a meniscus in said sample of blood at a second end of the microhematocrit capillary tube;
   ultrasonically coupling the first end of the microhematocrit capillary tube to the ultrasound transducer;
   forming standing waves in the blood sample by transmitting ultrasound energy into the blood sample from the ultrasound transducer and reflecting the ultrasound energy by the meniscus, the standing waves banding the blood sample into bands of packed red blood cells separated by bands of plasma.

* * * * *